United States Patent [19]
Vander Heyden et al.

[11] Patent Number: 5,820,260
[45] Date of Patent: Oct. 13, 1998

[54] MEASURING HEATING VALUE USING PREDETERMINED VOLUMES IN NON-CATIALYTIC COMBUSTION

[75] Inventors: William H. Vander Heyden, Mequon, Wis.; Ronald Arthur Berg, Tulsa, Okla.

[73] Assignee: Badger Meter, Inc., Milwaukee, Wis.

[21] Appl. No.: 731,403

[22] Filed: Oct. 18, 1996

Related U.S. Application Data

[63] Continuation-in-part of Ser. No. 682,828, Jul. 12, 1996.
[51] Int. Cl.$^6$ .................................................. G01N 25/22
[52] U.S. Cl. ................................................ 374/37; 374/36
[58] Field of Search ......................................... 374/36, 37

[56] References Cited

U.S. PATENT DOCUMENTS

| | | | |
|---|---|---|---|
| 4,351,614 | 9/1982 | Garnier | 374/37 |
| 4,533,258 | 8/1985 | Milovidov | 374/37 |
| 5,012,432 | 4/1991 | Stetter et al. | 364/557 |
| 5,165,884 | 11/1992 | Martin et al. | 431/7 |
| 5,201,581 | 4/1993 | Vander Heyden et al. | 374/37 |
| 5,226,728 | 7/1993 | Vander Heyden | 374/37 |
| 5,320,518 | 6/1994 | Stilger et al. | 431/7 |
| 5,482,679 | 1/1996 | Dijkstra et al. | 374/37 |

FOREIGN PATENT DOCUMENTS

| | | | |
|---|---|---|---|
| 0 304 266 A2 | 2/1989 | European Pat. Off. | |
| 0326494 | 8/1989 | European Pat. Off. | 374/37 |

*Primary Examiner*—Diego F. F. Gutierrez
*Attorney, Agent, or Firm*—Quarles & Brady

[57] ABSTRACT

The heating value of a sample gas is calculated by a microcontroller (12) from the heating value of a reference gas, and from an oxidation energy ratio determined as the gas is combusted by a flameless combustion process. The combustible gas is mixed with a combustion supporting gas, such as air, in a volume chamber (4) and injected into a combustion device (8, 50) in which a body of inert material (26, 51, 53) is heated above the auto-ignition temperature of the gas mixture. The inert material (26, 51, 53) is arranged to have a void dimension that is small enough to prevent the formation of an open flame during combustion. The process is repeated with a sample gas. During the injection cycle, the microcontroller (12) receives signals which monitor the power of combustion. The microcontroller (12) calculates the heating value of the sample gas and generates an output signal to a visual display or other output device.

32 Claims, 4 Drawing Sheets

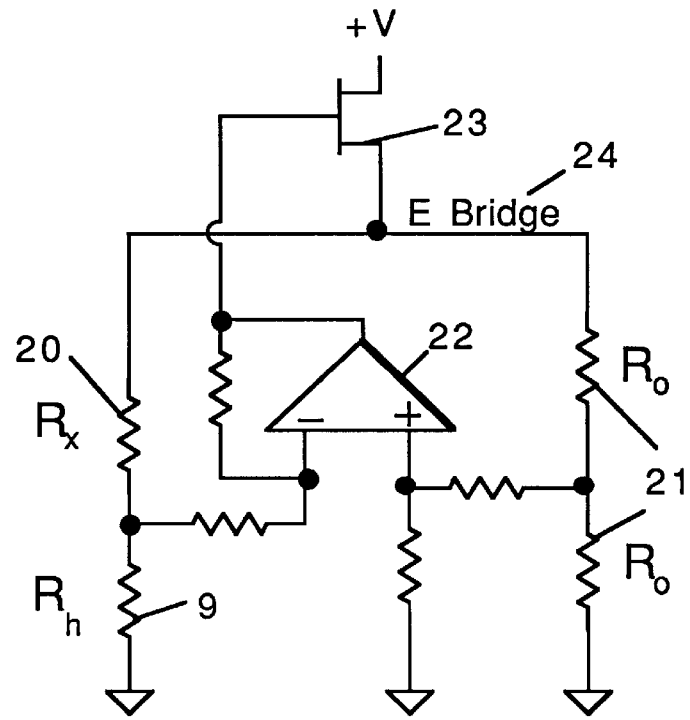
FIG. 2
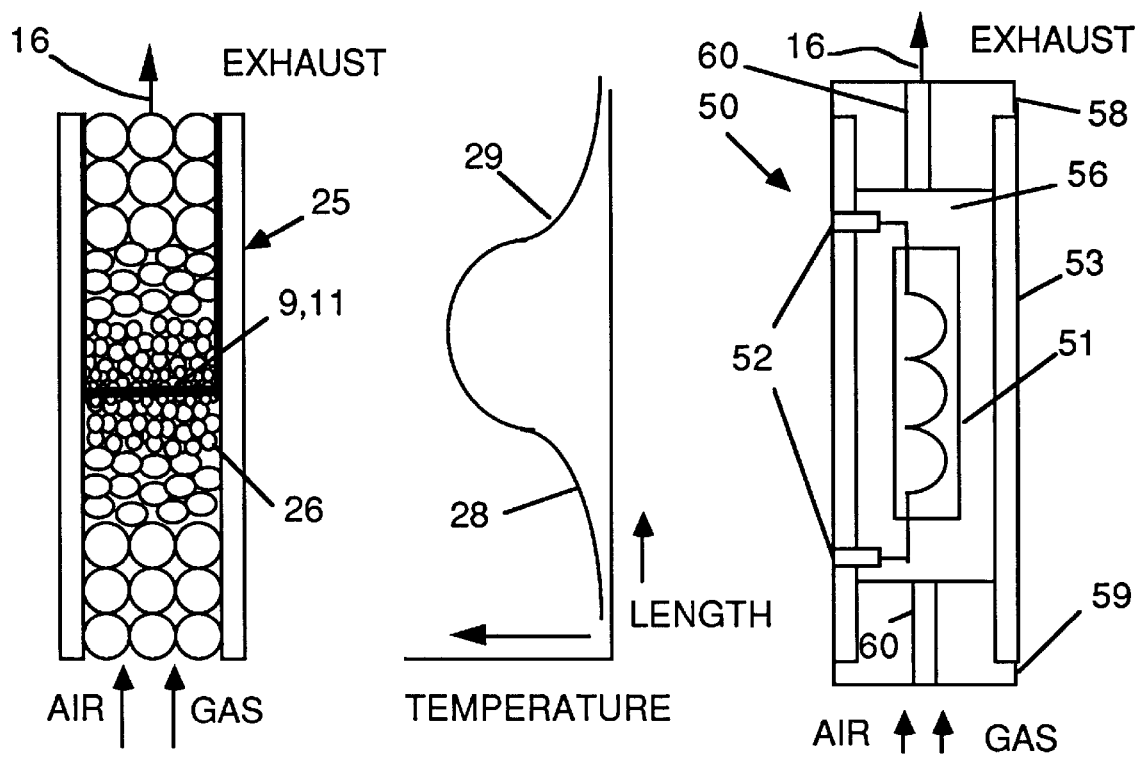
FIG. 3a     FIG. 3b     FIG. 3c

MEASURING HEATING VALUE USING PREDETERMINED VOLUMES IN NON-CATIALYTIC COMBUSTION

CROSS-REFERENCE TO RELATED APPLICATIONS

This is a continuation-in-part of our earlier copending U.S. application Ser. No. 08/682,828 filed Jul. 12, 1996.

TECHNICAL FIELD

The field of the invention is methods and apparatus for determining the heating value of gases.

DESCRIPTION OF THE BACKGROUND ART

The measurement of the heating value of natural gas is important in controlling combustion and is a necessary measurement in the distribution and sale of natural gas. There are four useful methods for measuring heating value.

The first method for measuring heating value is calorimetric measurement in which a volume of the gas is combusted. An amount of heat is liberated by the complete combustion and is carefully accumulated and measured. The amount of heat liberated is manifested by a change in temperature. This method is the original method employed and usually requires extreme control of flows and temperatures. The apparatus usually requires extensive maintenance.

The second method for measuring heating value is constituent analysis. Using a gas chromatography the fraction of each chemical constituent in the gas is determined. Then heating value is determined by summing the heating values for the individual constituents according to their fractional presence. The problem with constituent analysis is the reliability of the apparatus and its linearity. Gas chromatographs require constant maintenance and have a limited range for heating value measurement unless calibrated with a reference gas that is very similar to the sample gas.

The third method is stoichiometry, in which combustion is substantially completed with a perfect amount of oxygen. In this case, natural gases are combusted with air and the fuel-to-air ratio is adjusted until combustion results in either a maximum flame temperature or the stoichiometric point of perfect combustion, i.e., the knife edge at which there is no remaining oxygen.

Clingman, U.S. Pat. No. 3,777,562, is an example of the third method. In Clingman, heating value is measured by combustion of a gas with amounts of air that are adjusted to obtain the maximum flame temperature. This is further disclosed in Clingman, U.S. Pat. Nos. 4,062,236, 4,125,048 and 4,125,123. In each of these patents, the combustion of the air-gas mixture is accomplished with a combustion flame on a burner top and with a temperature sensing device such as a thermocouple. Certain environments cannot be served by equipment that presents an open flame.

The fourth method utilizes catalytic combustion. Gas is passed over a heated catalyst and oxidized. The amount of heat liberated can be measured either by temperature changes related to the catalytic reaction, by changes in power supplied to heat the catalyst or by measuring the temperature of the catalytic material. Catalytic combustion or catalytic oxidation is a known phenomenon with hydrocarbons. A mixture of hydrocarbon gas and air in the presence of platinum and/or palladium material will produce an oxidation reaction. The reaction occurs at temperatures below the auto-ignition temperature associated with a hydrocarbon. For example, methane when mixed with air will ignite at a temperature of about 730° C. and reach an open flame at a temperature exceeding 1600° C. Catalytic oxidation can take place at catalyst temperatures as low as 400° C. although efficient catalytic activity is achieved at temperatures near 500°–600° C.

One problem with catalytic oxidation is the potential for poisoning the catalyst. Certain chemicals such as sulfur or lead and numerous others, can combine with and disable a catalyst and therefore eliminate its usefulness in heating value measurement. In many processes, such as land fill gas recovery, the gases contain "poisons" in sufficient quantity to have a high probability of disabling the measurement process.

Another problem is the varied activation energy of the gas components which can introduce errors due to composition if only partial combustion is achieved.

SUMMARY OF THE INVENTION

The invention relates to apparatus and methods for measuring heating value of a combustible gas using a flameless combustion process.

The apparatus of the invention has a porous body of material with one or more spaces with linear dimensions that are less than a quenching dimension for the combustible gas; a heater element disposed in the porous body of material to heat a portion of the porous body of material to a temperature above the auto-ignition temperature of the combustible gas; a sensor for sensing the level of combustion and for generating a signal responsive thereto; and a processor responsive to signals from the sensor for calculating the heating value of the combustible gas.

The present invention utilizes a body of inert material for receiving and combusting mixtures of gases and a carrier gas, such as air. Under normal conditions, the gas would be oxidized or combusted and a flame would form.

A flame is an indication of oxidation or combustion, when the combustion products, $CO_2$ and $H_2O$ vapor, have insufficient heat capacity to carry away the heat of combustion by convection and conduction. The temperature of the combustion products therefore rises until the radiation heat loss is sufficient to balance the heat generated by oxidation. The temperature of the burned gases increases until the heat of combustion equals the heat losses. While conduction and convection rise in a linear relation to temperature, radiation losses respond in proportion to the fourth power of temperature, and provide an additional factor for stabilizing heat transfer rate. For natural gases, the temperature of the combustion products rise and reach radiation frequencies in the visible spectrum, i.e. the flame is visible but also it is very rich in non-visible infrared radiation.

In the present invention, inert material is formed in a body with only small voids, having a dimension that is less than the quenching dimension of the gas, so that an open flame is prevented by the quenching of rapid heat transfer.

The structure surrounding the small voids allows the heat transfer rate between the combustion gas products and the structure to be sufficiently high to prevent large temperature increases and to stabilize the temperature of the combustion products. The structure must have sufficient heat capacity to quench the flame without acquiring high levels of radiation.

In addition, the oxidation or combustion of the present invention can be performed with mixture concentrations over a wide range that extends from a very low level to a level beyond the stoichiometric mixture of the gas.

The gas combustion power or the combustion temperature, is measured as the gas mixture flows in the combustion device. A reference gas and a sample gas are measured in respective measurement cycles. The preferred embodiment compares oxidation energy of the sample gas and the reference gas at substantially an identical combustion temperature.

In the embodiments described herein, air flow is established well in excess of the air required to combust the gas, a lean gas condition. A predetermined volume of the reference gas is injected with the air. The reference gas/air is directed over or through the preheated column and the mixture is oxidized. Sensors are placed in the column to signal the temperature of combustion, which is then monitored along with combustion power level.

The reference gas cycle is followed by a the sample gas cycle, using the air flow rate condition described above. A pre-determined volume of the sample gas passes through the same heated structure and combustion energy is measured.

The ratio of the combustion energy of the sample gas to the combustion energy of the reference gas along with knowledge of the heating value of the reference gas allows computation of the heating value of the sample gas.

In the preferred embodiments of the invention, the inert material is non-catalytic. This allows the apparatus and the process of the invention to overcome the disadvantages of catalytic combustion, including possible "poisoning" of the catalyst, because no catalyst is used.

Other objects and advantages, besides those discussed above, will be apparent to those of ordinary skill in the art from the description of the preferred embodiment which follows. In the description, reference is made to the accompanying drawings, which form a part hereof, and which illustrate examples of the invention. Such examples, however, are not exhaustive of the various embodiments of the invention and, therefore, reference is made to the claims which follow the description for determining the scope of the invention.

BRIEF DESCRIPTION OF THE DRAWINGS

FIG. 2 is a detail schematic diagram of an electrical circuit in the catalytic apparatus of FIG. 1;

FIG. 3a is a schematic diagram of a first embodiment of a combustion device used in the apparatus of FIG. 1;

FIG. 3b is a graph of temperature versus longitudinal displacement within the combustion device of FIG. 3a;

FIG. 3c is a schematic diagram of a second embodiment of a combustion device used in the apparatus of FIG. 1;

DETAILED DESCRIPTION OF THE PREFERRED EMBODIMENTS

Figure 1:
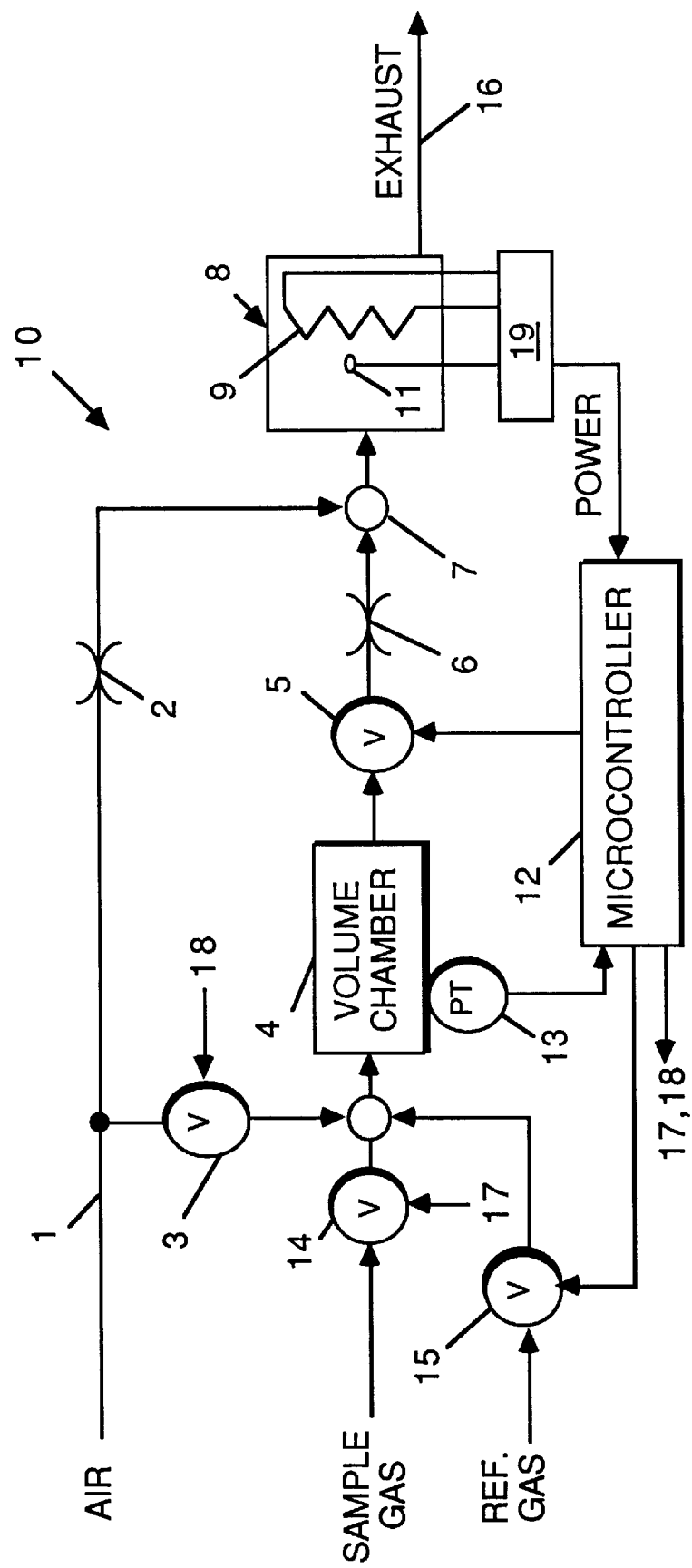
FIG. 1 is a block diagram of an apparatus for practicing the method of the present invention.

Referring to FIG. 1, an apparatus 10 for practicing the present invention has a combustion device 8 that receives air through supply line 1 from an external supply (AIR). In a first embodiment, combustion device 8 is provided by a body of porous inert solids 26 (see FIG. 3a). The porous body 26 is composed of material having high temperature and high heat capacity and is usually formed of ceramic materials.

Combustion device 8 also includes heater element 9 which is located at or in the central section of the porous material 26 to provide an initial starting temperature for the reaction. The temperature sensor 11 provides a signal proportional to the temperature at the reaction surface of the inert porous solids material.

Heater element 9 is energized by electricity from a power source 19 for heating the inert material to a temperature of 800° C. or more. Temperature sensor 11 is embedded in the inert material to sense the temperature at the reaction surface of this material. Temperature sensor 11 generates a signal as an input to power source 19. This signal is recognized by the power source 19 as representative of reaction temperature. From the combustion column 25 (FIG. 3a), an exhaust stream 16 is exhausted. This exhaust stream 16 includes the products of combustion. As is known in the art, additional steps may be taken to process the exhaust stream, however, these steps form no part of the present invention.

The flow rate of the air to column 25 of inert material is not critical. The flow rate can vary by +10% in a slow fashion, but it must be stable between a reference gas cycle and sample gas cycles. The air flow rate is also selected to create a lean flame condition. The air flow through supply line 1 creates a pressure drop across flow restrictor 2.

Microcontroller 12 is a suitable microelectronic CPU (central processing unit) with A-to-D and D-to-A interface circuitry. Microcontroller 12 operates by executing program instructions, some of which are represented by blocks in the flow chart in FIG. 5, the instructions being stored in a memory also represented generally by reference 12.

The apparatus more particularly includes on-off solenoid-operated valves 3, 14 and 15 for controlling and selecting sample gas or reference gas, respectively, to fill volume chamber 4. Microcomputer 12 connects to the valves 3, 14 and 15 shown in FIG. 1, including connections represented by reference numbers 17, 18. Solenoid valve 3 allows air from air supply 1 to flow through volume chamber 4 whenever solenoid valve 3 is activated. When not activated, valve 3 blocks air from volume chamber 4.

A reference gas supply (REF. GAS) is connected to control valve 15 which allows reference gas to enter volume chamber 4. The exit flow control valve 5 is also opened, allowing reference gas to flush volume chamber 4. After a sufficient delay to allow a complete flush, exit valve 5 is closed and chamber 4 is filled with a volume of reference gas. As gas pressure in volume chamber 4 reaches a predetermined pressure sensed by pressure transducer 13, inlet flow valve 15 is closed. The volume of gas in the volume chamber 4 is therefore a predetermined, known volume at a known temperature and pressure.

Following closure of valve 15, outlet control valve 5 is opened and air control valve 3 is opened, allowing flow of gas from volume chamber 5 through flow restrictor 6 and mixing with air flow at junction 7 and passing through the column 25 (FIG. 3a) in combustion device 8. When solenoid 3 is open, the air flow rate through volume chamber 4 is determined by the relative pressure loss flow rate relationship of restrictors 2 and 6. The flow rate ratio is usually set to achieve a lean mixture condition in time combustion device 8.

In this embodiment, the power source 10 uses a temperature sensor 11 to adjust the power that is supplied to heater 9 to maintain a constant temperature at sensor 11. Changes in this electrical power setting of the heater 9 are a measure of combustion energy or combustion temperature of the combusted gas on porous body 26. As time progresses, gas in volume chamber 4 is forced out by the air flow through valve 3. Microcontroller 12 monitors the energy of the combustion reaction in device 8. When microcontroller 12 has detected that all gas in the volume chamber 4 has been expelled, it signals control valve 5 to close, thereby stopping flow of gas to the combustion device 8. The flow of reference gas creates a pulse of combustion energy, which is sensed by monitoring the electrical power supplied to heater 9 and by sensing the temperature of combustion using sensor 11.

Control valve 14 is opened to fill volume chamber 4 with sample gas from a source (SAMPLE GAS). Valve 5 is also opened to allow flow through the volume chamber 4. After a period of time suitable to flush all reference gas and air out of volume chamber 4, valve 5 is closed. Flow into volume chamber 4 increases pressure in volume chamber 4 until a predetermined pressure in volume chamber 4 is reached, and then inlet flow control valve 14 is closed. The volume of gas in the volume chamber 4 is therefore a predetermined, known volume at a known temperature and pressure.

After closing valve 14, microcontroller 12 opens control valves 3, 5 to establish flow of sample gas through restrictor 6, through mixing point 7 and into combustion device 8, where sample gas is combusted in a cycle similar to the cycle with the reference gas. Power source 19 continuously adjusts power to heater 9 to maintain a constant temperature on sensor 11. As the gas flows, power changes to heater 9 represent the energy of gas combustion in the body of inert solids 26. These energy changes are integrated by microprocessor 12 to determine heating value.

In the illustrated embodiment, a single volume chamber is utilized, however other embodiments may advantageously utilize multiple chambers. The use of a single chamber simplifies the flow apparatus, however, the measurement process is slower, because the chamber must be exhausted of all gas at the end of each cycle before beginning the next cycle. The reference gas, for example, must be exhausted before the sample gas is introduced in volume chamber 4.

Next, microprocessor 12 computes the ratio of integrated energy detected for the sample gas and the reference gas and uses that ratio to compute the sample gas heating value as:

$$H_s = H_r \frac{\int \dot{E}_s dt}{\int \dot{E}_r dt} \tag{1}$$

where the subscripts r and s refer to heating value, H, for the reference and the sample conditions, respectively, and $\dot{E}$ is the energy rate or power of the gas combustion.

FIG. 2 depicts the electrical circuit of the power source 10, sensor 11 and heater 9 seen in FIG. 1. The circuit is a bridge which maintains a constant resistance by heating and cooling by electrical means.

In the preferred embodiments, resistance 9 in FIG. 2 is typically a platinum coiled-wire resistor. Platinum is selected due to its stable temperature coefficient over a wide temperature range. The resistance value R of resistance 9 can be expressed as follows:

$$R_h = R_{ho}(1 \alpha \Delta T) \tag{2}$$

Resistor 20 is a resistor whose value is selected to be the desired resistance of 9 at the temperature selected for the operation of the body of porous material 26. Resistance 9 is both the heater 9 for the combustion device 8 and the temperature sensor 11. Resistors 21 are a pair of resistors which divide the voltage 24 applied to the bridge. In FIG. 2, the resistors are shown as equal, however, this is not a strict requirement.

In FIG. 2, operational amplifier 22 senses the difference between the center tap voltages on each section of the bridge and amplifies that difference. The result is applied to power FET 23 and changes the voltage 24 on the bridge until the center tap voltages of the two sections become equal.

The temperature of heater/sensor 9, 11 is controlled to hold the temperature within a tolerance range of a commanded or set temperature. Electrical power is controlled as it is supplied to the heater/sensor 9, 11 to hold the resistance and temperature of heater/sensor 9, 11 within the tolerance range of the commanded or set temperature. When gas combustion takes place, the release of combustion energy tends to raise the temperature of heater 9 and sensor 11. The applied electrical power will be reduced a corresponding amount to maintain the commanded or set temperature of the heater/sensor 9, 11.

Because the combustion device 8 combusts the entire gas in the gas/air mixture, another embodiment can be made in which the electrical power to a heater 9 is maintained at a set value and the resulting temperature rise of the sensor 11 is measured and integrated. This can be made to function equally well with the constant temperature model and is deemed to be an equivalent thereof.

FIG. 3a depicts one construction of a combustion device 8 that includes a heater column 25 of porous inert material 26. Column 25 includes a tubular member that holds beads of ceramic material 26 which can be graduated in size as well as have a changing surface character to control emissivity of radiation components. This allows control of the heat transfer rate from the combustion products. An electrically powered heater 27 is located in the central region of the column 25 to heat the central section of the porous body 26 to at least the temperature of auto-ignition of the combustible gas.

The small voids in the porous body of solid material 26 are selected and characterized as having linear dimensions equal to or less than the quenching dimension of the gas flame. With methane, for example, the quenching dimension is about 2.5 millimeters (0.060"). The methane does not burn with an open flame when the voids in the body of solid materials 26 are equal to or less than 2.5 mm. Heat is transferred through the solid material 26 at a sufficient rate to prevent the large increases in temperature that would accompany an open flame.

Combustion produces combustion products such as $CO_2$ and $H_2O$ vapor. A flame is a visual indication that the combustion products have insufficient heat capacity to carry away the heat of combustion by convection and conduction alone. The temperature of the combustion products must then rise until the radiation level is high enough to radiate the excess heat. The rate of conduction and convection increases in linear relation to temperature. Radiation responds in proportion to the fourth power of temperature, and provides an additional and stabilizing factor to the heat transfer rate. The temperature of the burned gases increases until the heat of combustion equals the heat losses. For natural gases, the gas temperature reaches radiation frequencies in the visible spectrum and the flame is visible.

In the present invention, gas flow rates and volumes through the combustion apparatus 8 are also limited by design to limit the total available heat of the combustion reaction. If the energy available from combustion is too great, electrical power cannot be reduced enough to control the combustion. Therefore, limits are placed on the flow rates and volumes of the gas-air mixture to limit the heating power available by combustion to less than the electrical power required to heat the solid material 26 above the auto-ignition temperature.

The solids structure surrounding the small voids allows the heat transfer rate between the combustion gas products and the heater to be sufficiently high to prevent large temperature increases and thereby stabilize the combustion temperature. The body of material 26 must have sufficient heat transfer capacity to quench the flame without requiring high radiation temperatures.

The air and the gas are introduced at the base of the column 25 and travel through the ceramic material 26. Due to heat flow from the central section of column 25, the temperature curve 28 through of the inlet section of column 25, represented graphically in FIG. 3b, increases as the gas-air mixture flows toward the reaction zone at the center of the column 25.

After the reaction zone, the column section temperature cools, as represented by temperature curve 29, as the gases pass to the exhaust as shown in FIG. 3b.

When the air-gas mixture reaches the reaction zone, which has been heated to a temperature above the auto-ignition point, the gas oxidizes or combusts, releasing energy in the heat of combustion form. The released heat raises the temperature of the reaction zone and raises the resistance of the platinum heater 27. The power controller 19 (FIG. 1) for the heater 9 senses this increasing temperature and reduces the electrical excitation to maintain a constant temperature in the reaction zone. The change in electrical power corresponds to the increased combustion power or combustion temperature and is the indicator of combustion activity.

FIG. 3c illustrates a second embodiment of a combustion device 50. A heater/sensor element 51 is mounted within a tube 53 by spot welding the heater leads to posts 52. The dimensions between the heater body 51 and its surrounding tube 53 are maintained at under a flame quenching distance 56 End caps 58, 59 are also mounted close to heater 51 to quench flames. End caps 58, 59 have entry and exit passages 60 which are also equal to or less than a flame quenching dimension. As the gas mixture enters the combustion device 50, it contacts the heater 51, which is operated above the auto-ignition temperature, and the gas is combusted. The molecules of the gas disassociate and oxidize releasing the heat of oxidation and forming $CO_2$ and $H_2O$ vapor. The heat transfer rate due to conduction, convection and radiation control the combustion product gas temperatures by providing sufficient heat removal. As the gas exits the combustion device 50, the combustion gases and the excess air are cooled by the exit end cap 59 to a temperature well below the auto-ignition temperature.

Figure 4:
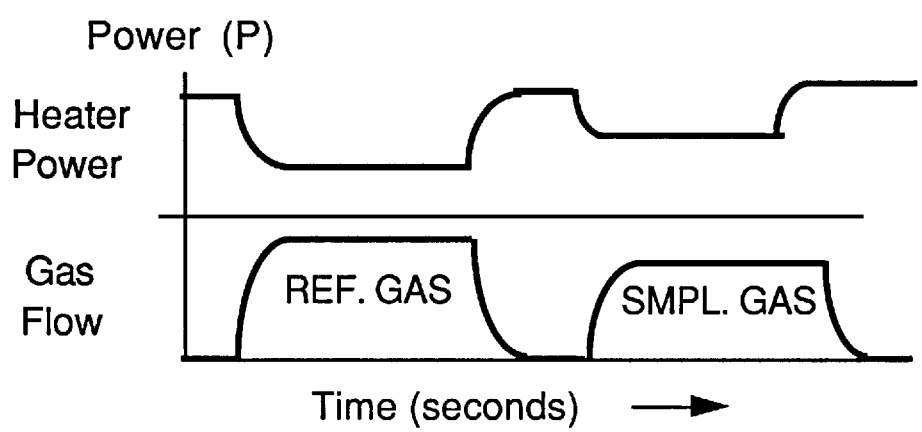
FIG. 4 illustrates graphs of heater power and gas flow versus time in the operation of the apparatus of FIG. 1.

FIG. 4 illustrates the effect of gas flow on heater electrical power for the embodiments described above. Initially, only air flows through the combustion device 8, 50, and consequently electrical heater power is at a maximum to provide a constant temperature in the reaction zone of the combustion device 8, 50. If desired, a baseline signal can be detected for heater power when only air is passing through the combustion device 8, 50. When reference gas flow is initiated, the mixture immediately oxidizes and the heater power is reduced to compensate. Generally, the flow of the reference gas/air mixture is at constant pressure. In time, the proportion of reference gas in the mixture reduces and ends, and heater power returns to a maximum. The heater electrical pulse during the reference gas cycle is measured and integrated, according to the denominator in the energy ratio in equation 1) above.

Then the sample gas flow is initiated, the mixture oxidizes and the heater power is reduced to compensate. Generally, the flow of the sample gas/air mixture is at constant pressure. In time, the proportion of sample gas in the mixture reduces and ends, and heater power returns to a maximum. The heater electrical pulse during the sample gas cycle is measured and integrated, according to the numerator in the energy ratio in equation 1) above. Since the heating value of the reference gas, $H_r$, is known, the three values needed to compute $H_s$ in Equation 1, are available, and the microcomputer can complete the calculation, and generate a signal to a suitable output device.

Figure 5:
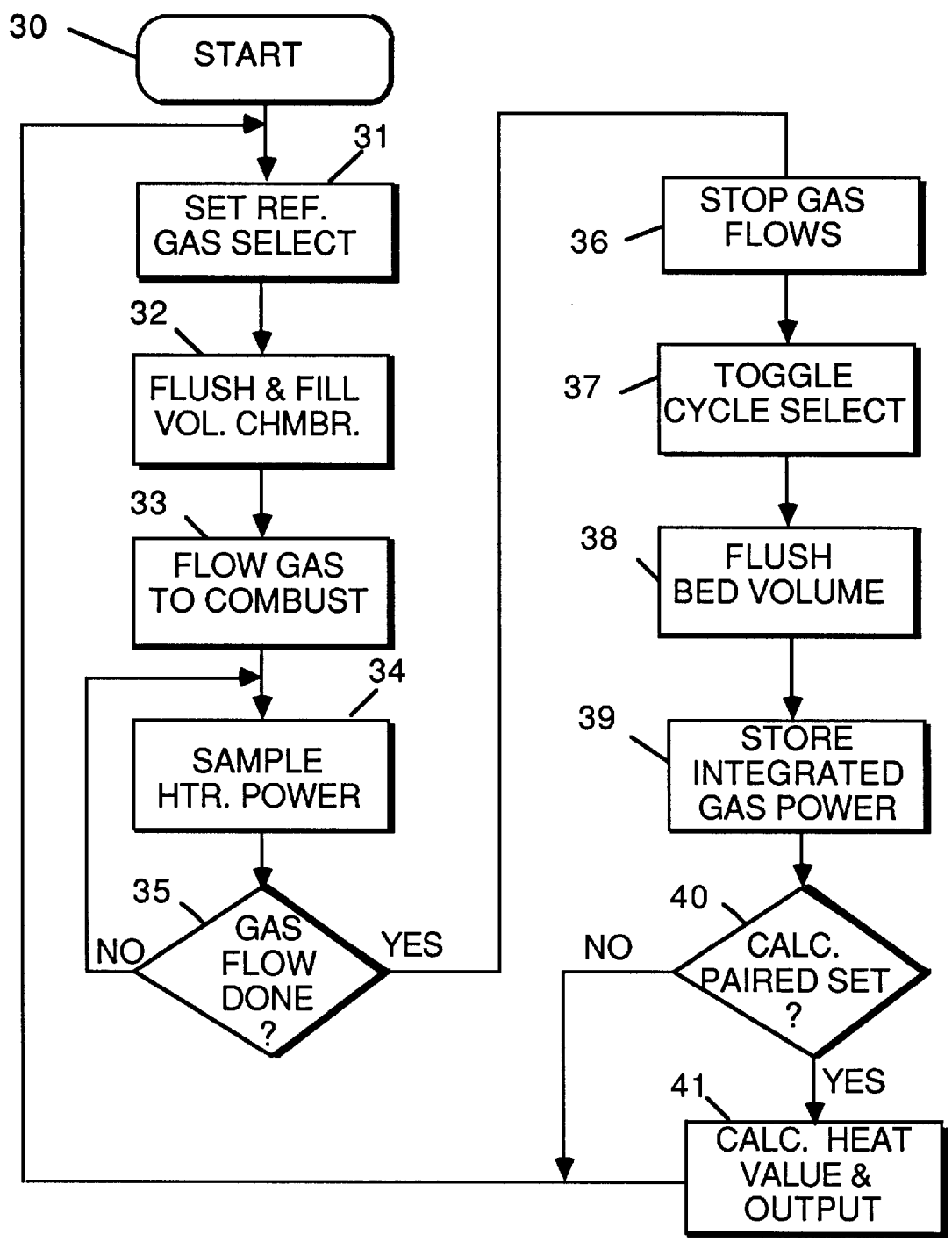
FIG. 5 is a flow chart of the operation of a microcontroller in the apparatus of FIG. 1.

FIG. 5 shows the operation from the viewpoint of the microcontroller 12 in executing its control program. The start of the operation is represented by start block 30. The microcontroller 12 executes instructions to select either the reference gas cycle or the sample gas cycle, as represented by process block 31. If the reference gas cycle is selected, the microcontroller 12 executes further instructions, represented by process block 32, to open valve 14 and allow reference gas to fill volume chamber 4 in preparation for the reference gas cycle. Next, as represented by process block 33, the microcontroller 12 executes further instructions to open valve 5 to allow reference gas to flow to the combustion device 8, 50. The microcontroller 12 then executes instructions represented by process block 34 to begin to detect changes in the electrical power ($\Delta P$) required by the combustion device 8, 50. The microcontroller 12 then executes instructions represented by decision block 35 to test for completion of gas flow. If the result is "NO," it loops back to continue with another sample. If the result is "YES," it proceeds to execute instructions represented by block 36 to end the first cycle and prepare for the next cycle.

As represented by process block 36, microcontroller 12 executes instructions to stop the gas flow of the reference gas by closing valve 15. The microcontroller 12 then executes instructions represented by process block 37 to change the selection to the other gas cycle. The microcontroller 12 then executes instructions represented by process block 38 to flush chamber 4 and combustion apparatus 8. Next, the microcontroller 12 then executes instructions represented by process block 39 to store the integrated power values for the cycle just completed. A check is then made, as represented by decision block 40, to see if both a reference cycle and a sample gas cycle have been completed within a recent time period. If the result is "YES," the data can be used calculate heating value as represented by process block 41. The heating value is then output to a visual display (not shown in FIG. 1) or another type of output device. If the data is not complete, the result from decision block 40 is "NO," and program returns to start a new gas measurement cycle, such as the sample gas cycle, at block 32.

This has been a description of examples of how the invention can be carried out. Those of ordinary skill in the art will recognize that various details may be modified in arriving at other detailed embodiments, and these embodiments will come within the scope of the invention.

Therefore, to apprise the public of the scope of the invention and the embodiments covered by the invention, the following claims are made.

We claim:

1. An apparatus for determining the heating value of a sample gas, the apparatus comprising:
   a heater structure of material containing at least one space with a linear dimension that is not greater than a quenching dimension for the sample gas so as to quench any flame produced by combustion of the sample gas;
   a heater element dispose din the heater structure of material to heat a portion of the heater structure of material to at least the auto-ignition temperature of the sample gas;

means for passing the sample gas into contact with the heater structure of material;

a sensor for sensing a power of combustion of the sample gas and for generating a signal responsive thereto; and a processor responsive to signals from the sensor for computing the heating value of the sample gas.

2. The apparatus of claim 1, wherein said material is a non-catalytic material.

3. The apparatus of claim 1, wherein said heater structure of material further comprises a plurality of solids arranged in a column with a plurality of spaces between said solids so as provided a porous body of material.

4. The apparatus of claim 3, wherein said spaces have a linear dimension not greater than about 2.5 mm.

5. The apparatus of claim 3, wherein said plurality of solids are beads of ceramic material.

6. The apparatus of claim 5, wherein said beads of ceramic material are graduated in size.

7. The apparatus of claim 6, wherein said ceramic material is a non-catalytic material.

8. The apparatus of claim 1, wherein said heater structure of material further comprises a casing and a body of ceramic material disposed in said casing;

wherein said heater element is disposed in said body of ceramic material; and wherein the heater structure of material has an interior space between said casing and said body of ceramic material with linear dimensions which are not greater than the quenching dimension for the sample gas.

9. The apparatus of claim 8, wherein the casing and the body of ceramic material are non-catalytic.

10. The apparatus of claim 9, wherein said heater element further comprises a coil of platinum wire contained in the body of ceramic material.

11. The apparatus of claim 8, wherein said spaces have a linear dimension not greater than about 2.5 mm.

12. The apparatus of claim 8, wherein said casing has opposite ends with an entrance for sample gas in one opposite end and an exit for sample gas in another opposite end and wherein said apparatus further comprises end caps disposed in said opposite ends of said casing, said end caps having passages with linear dimensions that are not greater than the quenching dimension for the sample gas.

13. The apparatus of claim 1, wherein:

the heater structure of material is heated to at least the auto-ignition temperature for combustion of the sample gas; and further comprising means for injecting a predetermined volume of the sample gas and a combustion supporting gas into contact with said heater structure of material to cause oxidation of said predetermined volume of said sample gas.

14. The apparatus of claim 13, further comprising means for limiting the gas flow rate of the sample gas to supply energy less than an amount of electrical power supplied to heat the portion of the heater structure of material.

15. The apparatus of claim 13, wherein said sensor further senses the electrical power supplied to the heater to maintain an approximately constant temperature in a region of combustion.

16. The apparatus of claim 13, wherein said combustion supporting gas is air.

17. The apparatus of claim 13, wherein said means for injecting included means of interrupting the flow of sample gas to flow only the combustion supporting gas into contact with the heater structure of material to establish a baseline value for measurement of combustion power.

18. The apparatus of claim 13, wherein the heated structure of material is formed of non-catalytic material.

19. The apparatus of claim 18, wherein said heated structure, of material further comprises a plurality of solids held together so as provide a porous body of solid material.

20. The apparatus of claim 18, wherein said heater element is enclosed by closely spaced walls for quenching any flame.

21. A method for determining the heating value of a sample gas, the method comprising:

heating a structure of material to at least the auto-ignition temperature of the sample gas;

passing the sample gas into contact with the heated structure of material;

combusting the sample gas within the heated structure of material while quenching any flame produced by said combustion;

sensing a power of combustion released by combustion of the sample gas; and computing the heating value of the sample gas in response to the power of combustion released by combustion of the sample gas.

22. The method of claim 21, wherein heating the structure of material includes heating non-catalytic material within the structure of material.

23. The method of claim 21, further comprising the steps of:

passing a reference gas into contact with the heated structure of material;

combusting the reference gas within the heated structure of material while quenching any flame produced by said combustion; and sensing a power of combustion released by combustion of the reference gas; and wherein computing the heating value of the sample gas includes using a known heating value of the reference gas, integrating the power of combustion of the sample gas and integrating the power of combustion of the reference gas.

24. The method of claim 21, wherein quenching any flame within the structure of material includes transferring heat from combustion of the sample gas to the structure of material at a rate sufficient for quenching any flame produced by said combustion.

25. The method of claim 21, further comprising the step of maintaining a sensor in the heated structure of material at approximately a constant temperature by adjusting the electrical power to a heater disposed in the heated structure of material.

26. The method of claim 21, further comprising the step of transmitting a signal representative of the heating value of the sample gas.

27. The method of claim 21, further comprising the step of limiting the supply of sample gas to supply less combustion energy than an amount of electrical energy supplied to heat the structure of material.

28. The method of claim 21, wherein sensing a power of combustion released by combustion of the sample gas includes sensing a signal from a sensor in the heated structure of material, and wherein said signal represents a reduction in electrical power required to maintain an approximately constant temperature of the sensor in the heated structure of material.

29. The method of claim 21, wherein said method is performed at ambient temperatures from approximately −40° F. to 130° F.

30. The method of claim 21, wherein the step of sensing a power of combustion released by combustion of the sample gas includes sensing a temperature of the heated structure of material through a constant resistance bridge circuit.

31. The method of claim 21, further comprising the step of flowing air only to the heated structure of material to establish a baseline sensor signal.

32. The method of claim 21, further comprising:

passing a reference gas into contact with the heated structure of material by injecting a known volume of a reference gas and a combustion supporting gas into contact with the heated structure of material;

combusting the reference gas within the heated structure of material while quenching any flame produced by said combustion;

sensing a power of combustion released by combustion of the reference gas;

wherein passing the sample gas includes injecting a known volume of a sample gas and a combustion supporting gas into contact with the heated structure of material;

and wherein the heating value of the sample gas is also computed in response to a known heating value of the reference gas and the power of combustion released by combustion of the reference gas.

* * * * *

UNITED STATES PATENT AND TRADEMARK OFFICE
CERTIFICATE OF CORRECTION

PATENT NO.   : 5,820,260
DATED        : October 13, 1998
INVENTOR(S)  : Vander Heyden, et al It is certified that error appears in the above-identified patent and that said Letters Patent is hereby corrected as shown below:

On the title page, item [57] Abstract, line 7, delete "in a volume chamber (4) and"

Signed and Sealed this

Twenty-third Day of February, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

PATENT NO. : 5,820,260
DATED : October 13, 1998
INVENTOR(S) : Vander Heyden et al.

It is certified that error appears in the above-identified patent and that said Letters Patent is hereby corrected as shown below:

On the title page, Item [54] and Column 1, line 3,
  "CATIALYTIC" should be --CATALYTIC--.

Column 1, line 30, "chromatography" should be --chromatograph--.

Column 1, line 50, "4,125,048" should be --4,125,018--.

Column 3, line 14, the second occurrence of "the" should be deleted.

Column 5, line 59, "$R_h = R_{ho} (1\alpha\Delta T)$" should be --$R_h = R_{ho} (1+\alpha\Delta T)$--.

UNITED STATES PATENT AND TRADEMARK OFFICE
CERTIFICATE OF CORRECTION

PATENT NO. : 5,820,260
DATED : October 13, 1998
INVENTOR(S) : Vander Heyden et al.

It is certified that error appears in the above-identified patent and that said Letters Patent is hereby corrected as shown below:

Column 8, line 64, "dispose din" should be --disposed in--.

Column 9, lines 11-12, "so as provided" should be --so as to provide--.

Signed and Sealed this

First Day of June, 1999

Attest:

Attesting Officer

Q. TODD DICKINSON

Acting Commissioner of Patents and Trademarks